United States Patent [19]

Levesque et al.

[11] Patent Number: 4,618,416
[45] Date of Patent: Oct. 21, 1986

[54] THIOAMIDES, THEIR PREPARATION AND USES

[75] Inventors: Guy Levesque, Contest; Pierre Tozzolino, Serres-Morlaas, both of France

[73] Assignee: Societe Nationale Elf Aquitaine (Production), France

[21] Appl. No.: 787,449

[22] Filed: Oct. 15, 1985

Related U.S. Application Data

[63] Continuation-in-part of Ser. No. 632,630, Jul. 19, 1984, abandoned.

[30] Foreign Application Priority Data

Jul. 19, 1983 [FR] France ............... 83 11880

[51] Int. Cl.$^4$ .................................... B03D 1/14
[52] U.S. Cl. .............................. 209/166; 252/61
[58] Field of Search .............. 209/166, 167; 252/61

[56] References Cited

U.S. PATENT DOCUMENTS

| | | | |
|---|---|---|---|
| 2,287,274 | 6/1942 | Ralsten et al. | 209/167 |
| 3,419,567 | 12/1968 | Wijma | 564/74 |
| 3,590,999 | 7/1971 | Gould et al. | 209/166 |
| 4,274,950 | 6/1981 | Larribau et al. | 252/61 |

FOREIGN PATENT DOCUMENTS 914553 3/1982 U.S.S.R. ............... 209/163

Primary Examiner—Bernard Nozick
Attorney, Agent, or Firm—Ostrolenk, Faber, Gerb & Soffen

[57] ABSTRACT

The froth flotation of a metal sulfide mineral is carried out using a thioamide as the collector in which the thioamide is of the formula

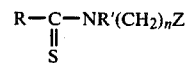

R designating $C_5$ to $C_{17}$ alkyls, R' being H or $(CH_2)_nOR''$ and n an integer of 1 to 6, while Z is —OR" or

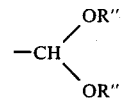

where R" means H, $CH_3$ or $C_2H_5$.

12 Claims, No Drawings

THIOAMIDES, THEIR PREPARATION AND USES

This is a continuation-in-part of application Ser. No. 632,630, filed July 19, 1984 now abandoned.

The invention relates to thioamides carrying a second function. It includes the use of such amides as collectors in the flotation of minerals. The invention also relates to certain new thioamides carrying a second function, as well as to a process for their preparation.

Thioamides have various industrial uses, for example as additives in cosmetic and pharmaceutical compositions, lubricating oil improvers, fungicides, vulcanization accelerators etc; they can also be used as collectors in the froth flotation of metal sulfide minerals such as, for example, galena, blende and pyrites. Flotation is carried out in the conventional fashion using a thioamide as the collector. The thioamides are of the formula

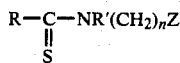

R designating $C_5$ to $C_{17}$ alkyls, R' being H or $(CH_2)_nOR''$ and n an integer of 1 to 6, while Z is —OR'' or

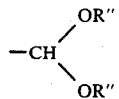

where R'' means H, $CH_3$ or $C_2H_5$.

The preferred manner of preparing the thioamide involves dissolving the thioester in a suitable solvent, which can be a chlorinated hydrocarbon, for example dichloromethane, dichloroethane, trichloroethane, trichloroethylene, tetrahydrofuran or other solvent inert as regards the reactants present; to the solution obtained, the selected amine is added, if required in a slight excess. The reaction is allowed to proceed during the necessary time, which varies with the nature of the reactants, but is generally from ½ to 6 hours. The temperature is from 0 degrees to 50 degrees C. and, preferably, between 0 degrees and 25 degrees C., except when R is a halogenated aryl group, in which case the preferred temperature is of the order of 40 degrees C.

Using this process, a series of new compounds have been prepared, within the scope of the present invention, constituted by thioamides which can be represented by the formula:

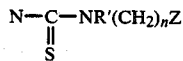

R designating $C_5$ to $C_{17}$ alkyls, R' being H or $(CH_2)_nOR''$ and n an integer of 1 to 6, while Z is —OR'' or

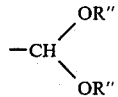

where R'' means H, $CH_3$ or $C_2H_5$. Preferably, R is a $C_7$ to $C_{11}$ linear alkyl group.

In the non-limitative examples which follow, the preparation of several of the products defined above is described. The physical properties of these compounds are set out in a Table at the end of the Examples. These thioamides and their homologues are utilizable successfully for the separation of minerals, particularly sulphur-containing minerals, by flotation.

EXAMPLES 1 TO 4

Synthesis of N-(2-hydroxyethyl)thiocarbamide

First a solution is prepared of 0.5 mole of the ethyl dithioate, $R—CS—SC_2H_5$, (where R is indicated below) in 100 ml of dichloromethane. 0.5 mole of ethanolamine, $NH_2CH_2CH_2OH$, is then added, with agitation, to the solution obtained. The mixture is allowed to stand at 25° C. for 3 hours. The solvent is then evaporated and the residue is crystallized and then re-purified by recrystallization from hexane, containing a trace of a polar solvent, particularly dichloromethane.

With this mode of operation, there have been prepared:

Ex. 1: R being $C_{11}H_{23}$, N-(2-hydroxyethyl)thiododecanamide $CH_3(CH_2)_{10}CS—NH—CH_2CH_2OH$. in a yield of 86%.

Ex. 2: R being $C_6H_5$, N-(2-hydroxyethyl)thiobenzamide $C_6H_5—CS—NH—CH_2CH_2OH$ in a yield of 45%.

Ex. 3: R being $CH_3O—C_6H_4$, N-(2-hydroxyethyl)-4-methoxy-thiobenzamide $CH_3O—C_6H_4—CS—NH—CH_2CH_2OH$ in a yield of 84%.

Ex. 4: R being $CH_3C_6H_4$, N-(2-hydroxyethyl)-4-methyl-thiobenzamide $CH_3—C_6H_4—CS—NH—CH_2CH_2OH$ in a yield of 69%.

EXAMPLE 5

Preparation of N-(3-aminopropyl)thiododecanamide 10.4 g of ethyl-dodecanedithioate is dissolved in 100 ml of toluene and the solution obtained is mixed with a solution of 30 g of 1,3-diaminopropane in 200 ml of toluene. The mixture is maintained at about 10° C. for 1 hour, with stirring.

The toluene is then distilled off under reduced pressure; the excess amine is eliminated by distillation. After recrystallization of the residue from hexane, pure N-(3-aminopropyl)dodecanethioamide, $CH_3(CH_2)_{10}—C—S—NH—CH_2CH_2CH_2NH_2$, is obtained in a yield of 45%.

EXAMPLES 6 TO 10

Preparation of N-(6-aminohexyl)thioamides

The operative mode consists of adding 0.5 mole of the selected alkyl dithioate. $R—CS—SR'$, diluted with 100 ml of toluene, to 200 ml of a toluene solution of 0.5 mole of 1,6-diaminohexane.

The disappearance of the colour of the thioester allows the reaction to be followed; this is generally terminated after 30 minutes at 25° C. Exceptionally, in the case of Example 9, 1 hour at 40° C. was required. The toluene and the major part of the excess amine are eliminated by distillation under reduced pressure, in order to be re-used in a new preparation after separation of the mercaptan formed. The residue from the distillation is washed with a small quantity of water, which causes elimination of the remaining amine.

For the compounds below, the residue was redissolved in toluene and dry HCl gas was passed into the solution obtained, thus causing precipitation of the hydrochloride of the thioamide formed.

| Ex. No | Thioester used | Thioamide obtained | % Yield based on the thioester |
|---|---|---|---|
| 6 | Ethyl decanedithioate | $C_9H_{19}CS-NH(CH_2)_6NH_2 \cdot HCl$ | 91 |
| 7 | Methyl benzenedithioate | $C_6H_5CS-NH(CH_2)_6NH_2 \cdot HCl$ | 62 |
| 8 | Ethyl-para-methoxy-benzene-dithioate | $CH_3(para)$<br>$\|$<br>$O$<br>$\|$<br>$C_6H_4CS-NH(CH_2)_6NH_2 \cdot HCl$ | 64 |
| 9 | Ethyl-para-chloro-benzene dithioate | $Cl(para)$<br>$\|$<br>$C_6H_4CS-NH(CH_2)_6NH_2 \cdot HCl$ | 25 |
| 10 | Methyl-para-methyl-benzene dithioate | $CH_3$<br>$\|$<br>$C_6H_4CS-NH(CH_2)_6NH_2 \cdot HCl$ | 67 |

Similar results are obtained starting from the corresponding monothioic esters: $R-C^S-OR'$.

EXAMPLES 11 AND 12

Thioamides of N-(2-dimethylamino-ethane)

The operative mode of the foregoing Examples is used with N,N-dimethylethylenediamine, $(CH_3)_2N-CH_2CH_2-NH_2$, which is reacted with an O-alkyl thioester $R-CS-OR'$.

11. The thioester employed, ethyl decanethioate, $CH_3(CH_2)_8-CS-OC_2H_5$, gives N-(2-dimethylamino-ethyl)-thiodecanamide,

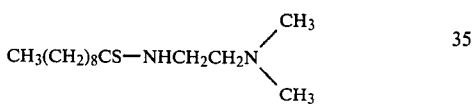

in a yield of 81%. The same result is obtained starting from ethyl decanedithioate $CH_3(CH_2)_8CS-SC_2H_5$.

12. Starting with ethyl para-chlorobenzenedithioate, $Cl-C_6H_4CS-SC_2H_5$, N-(2-dimethylamino-ethyl)-4-chlorothiobenzamide,

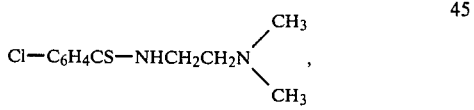

is obtained, the yield being 68%.

EXAMPLES 13 & 14

Preparation of N-(2,2-dimethoxyethyl)thioamides

Operation is as in Examples 1 to 4, but with ethanolamine replaced by 2,2-dimethoxyethylamine,

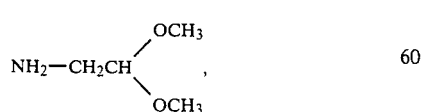

which leads to thioamides carrying acetal functions, as follows:

13. Starting from the ethyl ester of decanethioic acid, $C_9H_{19}CS-OC_2H_5$, N-(2,2-dimethoxyethyl-)thiodecanamide,

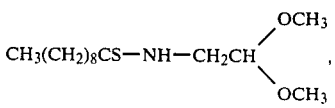

is obtained.

14. Starting from ethyl p.chloro-benzene-dithioate, N-(2,2-dimethoxyethyl)-4-chlorothiobenzamide,

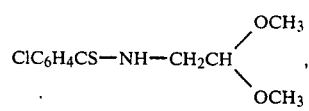

is made, in a yield of 57%.

EXAMPLE 15

Preparation of a thioamide having a carboxyl function

The amine utilized here is an amino acid. 0.2 mole of DL-alanine,

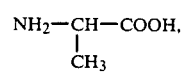

is added in small portions to 300 ml of a 10% aqueous solution of NaOH in which has been dissolved 0.2 mole of methyl octanedithioate, $CH_3(CH_2)_6CS-SCH_3$. The mixture is maintained at the ambient temperature for 15 hours. It is then acidified with 300 ml of 20% aqueous HCl acid, which causes precipitation of the thioamide formed. The latter is purified by recrystallization from hexane containing a slight amount of ether. N-(2-carboxyethyl)thio-octamide,

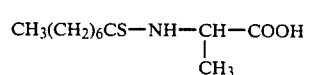

is thus obtained in a yield of 76% in relation to the thioester used.

EXAMPLES 16 TO 18

Thioamides carrying a pyridyl group

The selected dithioesters are reacted with 2-aminomethylpyridine (or α-amino-picoline)

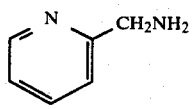

following the technique of Examples 1 to 4.

The dithioesters utilised are respectively those of Examples 8, 9 and 10 indicated above and the following thioamides are obtained:

16. N-(2-pyridylmethyl)-4-methoxythiobenzamide,

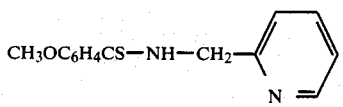

in a 60% yield.

17. N-(2-pyridylmethyl)-4-chlorothiobenzamide, in a 54% yield.
18. N-(2-pyridylmethyl)-4-methylthiobenzamide, in a 58% yield.

EXAMPLE 19

Preparation of a thioamide carrying two hydroxyl substituents on the nitrogen, particularly N-bis(2-hydroxyethyl)dodecanethioamide,

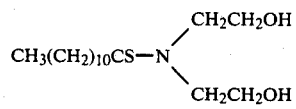

The mixture of 0.2 mole of ethyl dodecanedithioate with 0.24 mole of diethanolamine is heated to 160° C. for 30 minutes. After cooling, an equal volume of water is added; the whole is then cooled to cause separation of an oil; this treatment is renewable to eliminate the excess diethanolamine.

The thioamide obtained, having the formula given above, is an oil slightly soluble in water. The operative conditions are similar to those used with the other dialkanolamines.

EXAMPLE 20

Production of a thioamide having a carboxyl group on the nitrogen.

18 g of 2-aminopropionic acid ($\beta$-alanine) is dissolved in 100 ml of 10% aqueous caustic soda; 21 g of ethyl octanedithioate in 200 ml of tetrahydrofuran is then added; the mixture is agitated for 48 hours and then the organic solvent is distilled off. After cooling, the mixture is acidified with 200 ml of 20% hydrochloric acid; the precipitate which forms is separated and then washed with 1% HCl and with water. After drying, it can be recrystallized from toluene.

$CH_3-(CH_2)_6-CS-NH-CH_2CH_2-CO_2H$ Yield 73%

MELTING POINTS OF THIOAMIDES R—C(=S)—NH—R″Z

| Ex. no | R | R″ | Z | MP °C. |
|---|---|---|---|---|
| 1 | $CH_3(CH_2)_{10}-$ | $-CH_2CH_2-$ | $-OH$ | 53 |
| 2 | $C_6H_5-$ | " | " | 94 |
| 3 | $CH_3OC_6H_4-$ | " | " | 97 |
| 4 | $CH_3C_6H_4-$ | " | " | 122 |
| 5 | $CH_3(CH_2)_{10}-$ | $-CH_2CH_2CH_2-$ | $-NH_2$ | 104 |
| 6 | $CH_3(CH_2)_8-$ | $-(CH_2)_6-$ | $-NH_2.HCl$ | 168 |
| 7 | $C_6H_5-$ | " | " | 125 |
| 8 | $p.CH_3OC_6H_4-$ | " | " | 179 |
| 9 | $p.Cl-C_6H_4-$ | " | " | 173 |
| 10 | $p.CH_3-C_6H_4$ | " | " | 155 |
| 11 | $CH_3(CH_2)_8-$ | $-CH_2CH_2-$ | $-N(CH_3)_2$ | 38 |
| 12 | $p.Cl-C_6H_4-$ | " | " | 82 |
| 13 | $CH_3(CH_2)_8-$ | $-CH_2-$ | $-CH(OCH_3)_2$ | 22 |
| 14 | $p.Cl-C_6H_4-$ | " | " | 34 |
| 15 | $CH_3(CH_2)_6-$ | $-CH(CH_3)-$ | $-COOH$ | Decomp. |

-continued

MELTING POINTS OF THIOAMIDES R—C(=S)—NH—R''Z

| Ex. no | R | R'' | Z | MP °C. |
|---|---|---|---|---|
| 16 | p.CH$_3$OC$_6$H$_4$ | —CH$_2$— | pyridyl | 94 |
| 17 | p.Cl—C$_6$H$_4$— | —CH$_2$— | pyridyl | 106 |
| 18 | p.CH$_3$—C$_6$H$_4$ | " | " | 81 |
| 19 | CH$_3$(CH$_2$)$_{10}$— | " | —N(CH$_2$CH$_2$OH)$_2$ | oil |
| 20 | CH$_3$(CH$_2$)$_6$— | —CH$_2$CH$_2$— | —COOH | 93 |

The thioamides according to the invention are suitable for the usual uses of thioamides. They can be utilized for the protection of plants against parasites. In an interesting application, the thioamide serves as the collector for the flotation of minerals, as illustrated by Example 21 below.

EXAMPLE 21

Flotation tests in a HALLIMOND cell are effected in the standard manner, described in French published patent No. 2429613, page 3, lines 26 to 40. The collector employed is N-bis(2-hydroxyethyl)dodecanethioamide of Example 19 given above. It is utilized in a 1% ethanolic solution at the rate of 100 g of collector per tonne of mineral.

The percentages of the minerals flotated at different pH values are as follows:

| pH | Galena | Blende | Pyrites |
|---|---|---|---|
| 5.5 | 93% | 82% | 40% |
| 7.02 | 91 | 80 | 56 |
| 9.01 | 84 | 13 | 23 |
| 10.5 | 82 | 12 | 11 |

It can be seen that up to pH 7 the results with galena are remarkable and they are very good with blende. Starting at pH 9, the separation of these two minerals is very easy. The thioamide also proves to be useful for the separation of pyrites. This collector is also suitable in the case of chalcopyrite.

EXAMPLES 22 by 37

Flotation tests were carried out in the manner described in Example 21 with various thioamides belonging to the group of compounds having the formula $$R-C(=S)-NH-(CH_2)_nOH,$$

the pulp of the mineral treated having the pH 6.7.

| N° Example | Alkyl R | n | % of mineral recovered galena | blende |
|---|---|---|---|---|
| 22 | C$_3$H$_7$ | 2 | 63 | 58 |
| 23 | C$_4$H$_9$ | 2 | 67 | 58 |
| 24 | C$_5$H$_{11}$ | 2 | 78 | 72 |
| 25 | C$_7$H$_{15}$ | 2 | 88 | 79 |
| 26 | C$_7$H$_{15}$ | 3 | 87 | 77 |
| 27 | C$_8$H$_{17}$ | 2 | 89 | 81 |
| 28 | C$_9$H$_{19}$ | 1 | 88 | 80 |
| 29 | C$_9$H$_{19}$ | 2 | 89 | 78 |
| 30 | C$_9$H$_{19}$ | 4 | 87 | 78 |
| 31 | C$_{11}$H$_{23}$ | 3 | 92 | 82 |
| 32 | C$_{13}$H$_{27}$ | 2 | 90 | 79 |
| 33 | C$_{15}$H$_{31}$ | 2 | 91 | 78 |
| 34 | C$_{15}$H$_{31}$ | 4 | 90 | 80 |
| 35 | C$_{17}$H$_{35}$ | 1 | 88 | 76 |
| 36 | C$_{19}$H$_{39}$ | 2 | 74 | 61 |
| 37 | C$_{19}$H$_{39}$ | 3 | 72 | 60 |

As seen very good results are obtained in examples 24 to 35, while the rate of mineral recovery has decreased in examples 22, 23, 36 and 37. That means best collectors are those in which R is an alkyl of C$_5$ to C$_{17}$ or—in other words—the thioamide group R—CS—NH— has 6 to 18 carbon atoms.

EXAMPLES 38-44

Flotation tests, similar to those of preceding examples, were carried out with different thioamides having two OH in their substitution group. They are characterized by the formula $$R-C(=S)-N((CH_2)_nOH)_2$$

The following recovery rates were obtained.

| Example N° | Alkyl R | n | % of mineral recovered galena | blende |
|---|---|---|---|---|
| 38 | C$_3$H$_7$ | 2 | 66 | 61 |
| 39 | C$_5$H$_{11}$ | 2 | 80 | 74 |
| 40 | C$_9$H$_{19}$ | 1 | 90 | 81 |

-continued

| Example N° | Alkyl R | n | % of mineral recovered galena | blende |
|---|---|---|---|---|
| 41 | C9H19 | 2 | 91 | 83 |
| 42 | C9H19 | 3 | 89 | 80 |
| 43 | C17H35 | 3 | 90 | 78 |
| 44 | C19H39 | 2 | 73 | 63 |

While the above results show that the presence of a second OH in the molecule of thioamide somewhat improves the flotation, they confirm the conclusion from examples 21-37 that commercially best collectors are those in which R has 5 to 17 carbon atoms.

EXAMPLES 45-49

Flotation experiments were carried out with a fine powder of a mineral 90% of which pass the US sieve n° 140 (ASTM E-11-61), that means have dimensions less than 105 microns. The mineral originated from French Pyrenean region and had 4, 8% Pb and 12, 1% Zn in sulfide from.

The powder is froth flotated during 15 minutes in an industrial flotation cell of 125 liters. The pH of the pulp treated is 7.5. 25 grams of methyl isobutyl carbinol per ton of mineral are added as foaming agent. Each of the collectors studied is used at the rate of 0.132 moles per ton of mineral; the corresponding amounts expressed in grams per ton (g/t) are given in the following Table of results, which shows the % of Pb and Zn recovered.

| Ex. | collector | g/t | % Pb | % Zn |
|---|---|---|---|---|
| 45 | $C_{11}H_{23}CSNHCH_2CH_2OH$ N—(2-hydroxyethyl) thiododecanamide | 35 | 92.4 | 82.8 |
| 46 | $C_9H_{19}CSNHCH_2CH(OCH_3)_2$ N—(2,2-dimethoxyethyl) thiodecanamide | 35 | 91.3 | 83.9 |
| 47 | $C_9H_{19}CSNHCH_2CH_2OC_2H_5$ N—(2-ethoxyethyl) thio-decanamide | 33 | 90.7 | 83.5 |
| 48 | $C_{11}H_{23}CSN(CH_2CH_2OH)_2$ N—bis (2-hydroxyethyl) thiododecane-amide | 40 | 93.2 | 86.1 |
| 49 | Potassium amyl-xanthate: "PAX" | 20 | 86.7 | 78.8 |

As seen the collectors according to the invention, 45 by 48, give quite better results than one of the best usual collectors, the PAX, does.

EXAMPLE 50

The compound of example 45, that means $C_{11}H_{23}CSNHCH_2CH_2OH$ has been tested as froth flotation collector in a Halimond cell following the procedure described in U.S. Pat. No. 4,274,950, col.3, with a mineral which contains galena, blende, chalcopyrite and pyrite. The flotation is effected with pulps having different pH.

Here are the rates of recovery of each of the above minerals.

| pH | % recovered Galena | Blende | Chalcopyrite | Pyrite |
|---|---|---|---|---|
| 5.5 | 94 | 87 | 68 | 36 |
| 7.5 | 93 | 81 | 57 | 52 |
| 9.0 | 89 | 28 | 53 | 21 |
| 10.5 | 82 | 21 | 50 | 12 |

EXAMPLE 51

By the same method as in Example 50, N-(2,2-dimethoxyethyl)thiodecanamide, i.e. $C_9H_{19}CSNHCH_2CH_2(OCH_3)_2$ is tried as collector. The following results are obtained.

| pH | % recovered Galena | Blende | Chalcopyrite | Pyrite |
|---|---|---|---|---|
| 5.5 | 89 | 58 | 78 | 44 |
| 7.5 | 86 | 44 | 69 | 28 |
| 9.0 | 83 | 22 | 62 | 27 |
| 10.5 | 82 | 18 | 59 | 22 |

The above examples show that it is possible to choose a collector according to the invention and use it at an appropriate pH, that certain of the mineral components be enriched with respect to others.

What is claimed is:

1. Process of froth flotation of metal sulfide minerals in which a thioamide is employed as the collector and the metal sulfide is recovered from the froth, wherein the thioamide is of the formula

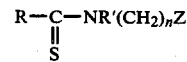

R designating $C_5$ to $C_{17}$ alkyls, R' being H or $(CH_2)_nOR''$ and n an integer of 1 to 6, while Z is —OR'' or

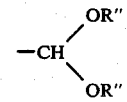

where R'' means H, $CH_3$ or $C_2H_5$.

2. Process according to claim 1, wherein the collector is N-(2-hydroxyethyl)-thiodecanamide.

3. Process according to claim 1, in which the collector is N-(2-hydroxyethyl)-thiodecanamide.

4. Process according to claim 1, in which the collector is N-bis(2-hydroxyethyl)-thiodecanamide.

5. Process according to claim 1, in which the collector is N-(2-methoxyethyl)-thiodecanamide.

6. Process according to claim 1, in which the collector is N-(2,2-dimethoxyethyl)thiodecanamide.

7. Process according to claim 1, in which the collector is N-(2-methoxyethyl)-thiodecanamide.

8. Process according to claim 1, in which the collector is N-bis(2-methoxyethyl)-thiodecanamide.

9. Process according to claim 1, wherein n is 1 or 2.

10. Process according to claim 9, wherein R is a $C_7$ to $C_{11}$ linear alkyl.

11. Process according to claim 10, wherein R'' is H.

12. Process according to claim 10, wherein R'' is $CH_3$.

* * * * *